US007381789B2

(12) United States Patent
Kumar

(10) Patent No.: US 7,381,789 B2
(45) Date of Patent: Jun. 3, 2008

(54) SYNTHESIS OF INORGANIC STRUCTURES USING TEMPLATION AND CATALYSIS BY SELF ASSEMBLED REPEAT PROTEIN POLYMERS

(75) Inventor: Manoj Kumar, Fremont, CA (US)

(73) Assignee: Genencor International, Inc., Alto, CA (US)

( * ) Notice: Subject to any disclaimer, the term of this patent is extended or adjusted under 35 U.S.C. 154(b) by 421 days.

(21) Appl. No.: 10/441,965

(22) Filed: May 20, 2003

(65) Prior Publication Data
US 2004/0014186 A1    Jan. 22, 2004

Related U.S. Application Data

(60) Provisional application No. 60/381,913, filed on May 20, 2002.

(51) Int. Cl.
    *C07K 17/00*      (2006.01)
(52) U.S. Cl. .................. 530/300; 530/420; 977/715
(58) Field of Classification Search ............... None
    See application file for complete search history.

(56) References Cited

U.S. PATENT DOCUMENTS

| | | | |
|---|---|---|---|
| 4,516,276 | A | 5/1985 | Mittelmeier et al. |
| 5,243,038 | A | 9/1993 | Ferrari et al. |
| 5,412,074 | A | 5/1995 | Jones et al. |
| 5,626,853 | A | 5/1997 | Bara et al. |
| 5,627,148 | A | 5/1997 | Dubief et al. |
| 5,679,543 | A | 10/1997 | Lawlis |
| 6,004,444 | A | 12/1999 | Aksay et al. |
| 6,018,030 | A | 1/2000 | Ferrari et al. |
| 6,034,220 | A | 3/2000 | Stedronsky |
| 6,153,602 | A | 11/2000 | Dubief et al. |
| 6,184,348 | B1 | 2/2001 | Ferrari et al. |
| 6,228,248 | B1 | 5/2001 | Aksay et al. |
| 6,355,776 | B1 | 3/2002 | Ferrari et al. |
| 6,358,501 | B1 | 3/2002 | Dietz et al. |
| 6,365,661 | B1 | 4/2002 | Fischer et al. |
| 6,365,877 | B1 | 4/2002 | Chen et al. |
| 6,368,606 | B1 | 4/2002 | Dubief et al. |
| 6,670,438 | B1 * | 12/2003 | Morse et al. ............ 528/21 |
| 2001/0006664 | A1 | 7/2001 | Ensley |
| 2001/0013294 | A1 | 8/2001 | Bruno et al. |
| 2001/0027570 | A1 | 10/2001 | Blees |
| 2002/0064539 | A1 | 5/2002 | Philippe et al. |

FOREIGN PATENT DOCUMENTS

| | | |
|---|---|---|
| EP | 0 540 357 A2 | 5/1993 |
| EP | 0 699 431 A1 | 3/1996 |
| WO | WO 00/35993 | 6/2000 |
| WO | WO 01/46213 A2 | 6/2001 |
| WO | WO 01/87825 A1 | 11/2001 |

OTHER PUBLICATIONS

Cha, J. et al. Nature 403: 289-292 (Jan. 2000).*
Sarikaya et al.,"Molecular biomimetics: nanotechnology through biology", Nature Materials 2: 577-585 (Sep. 2003).*
McMilan et al., "Ordered nanoparticle arrays formed on engineered chaperonin protein templates", Nature Materials 1: 247-252 (Dec. 2002).*

Deming, Facile synthesis of block copolypeptides of defined architecture, Nature, vol. 390, Nov. 27, 1997, pp. 386-389.
Fan, et al., Rapid prototyping of patterned functional nanostructures, Nature, vol. 405, May 4, 2000, pp. 56-60.
Brott et al., Ultrafast holographic nanopatterning of biocatalytically formed silica, Nature, vol. 413, Sep. 20, 2001, pp. 291-293.
Huo et al., Generalized synthesis of periodic surfactant/Inorganic composite materials, Nature, vol. 368, Mar. 24, 1994, pp. 317-321.
Zhou et al, Efficient Catalysis of Polysiloxane Synthesis by Silicatein α Requires Specific Hydroxy and Imidazole Functionalities, Angew. Chem. Inst., Ed. 1999, 38, No. 6, pp. 779-782.
Gosline et al., Elastic proteins: biological roles and mechanical properties, The Royal Society, Feb. 28, 2002, pp. 121-132.
Kroger et al., Polycationic Peptides from Diatom Biosilica That Direct Silica Nanosphere Formation, Science, vol. 286, Nov. 5, 1999, pp. 1129-1132.
Naik et al., Silica-Precipitating Peptides Isolated from a Combinatorial Phage Display Peptide Library, Journal of Nanoscience and Nanotechnology, 2002, vol. 2, No. 1, pp. 95-100.
Kroger et al, Silica-precipitating Peptides from Diatoms, The Chemical Structure of Silaffin-1A From Cylindrotheca Fusiformis, J. Biol. Chem., vol. 276, Issue 28, 26066-26070, Jul. 13, 2001, pp. 1-12.
Mizutani et al., Silicic Acid Polymerization Catalyzed by Amines and Polyamines, Bull. Chem. Soc. Jpn., 71, 2017-2022 (1998).
Mizutani et al., Silicic Acid Polymerization Catalyzed by Amines and Polyamines, Chemistry Letters, 1998 pp. 133-134.
Hartgerink et al., Peptide-amphiphile nanofibers: A versatile scaffold for the preparation of self-assembling materials, PNAS, Apr. 16, 2002, vol. 99, No. 8, pp. 5133-5138.
Zhang, Emerging biological materials through molecular self-assembly, Elsevier, Biotechnology Advances 20 (2002) pp. 321-339.
Wong et al., Assembly of Nanoparticles into Hollow Spheres Using Block Copolypeptides, Nano Letters, vol. 0, No. 0, pp. A-E.
Arkles, Commercial Applications of Sol-Gel-Derived Hybrid Materials, Mrs Bulletin, May 2001, pp. 402-408.
Sarikaya, Biomimetics: Materials fabrication through biology, PNAS, Dec. 7, 1999, vol. 96, No. 25, pp. 14183-14185.
Alvarez, Engineering Protein Molecules for the Ordered Structuring of Silica, National Nanofabrication Users Network, pp. 82-83.
Coradin et al., Biogenic Silica Patterning: Simple Chemistry or Subtle Biology? ChemBioChem 2003, 3, pp. 1-9.
Aksay I.A. et al., "Biomimetic Pathways for Assembling Inorganic Thin Films" Science, American Assoc. for the Advancement of Science, US, vol. 273, Aug. 16, 1996, pp. 892-898.
Bunker B.C. et al., "Ceramic Thin-Film Formation on Functionalized Interfaces Through Biomimetic Processing" Science, American Assoc. for the Advancement of Science, US, vol. 264, Apr. 1, 1994, pp. 48-55.
Weiner S. et al., "Organization of Extracellularly Mineralized Tissues: A Comparative Study of Biological Crystal Growth" Critical Reviews in Biochemistry, vol. 20, No. 4, 1986, pp. 365-408.

* cited by examiner

*Primary Examiner*—Robert Mondesi
*Assistant Examiner*—Anand Desai
(74) *Attorney, Agent, or Firm*—Dinsmore & Shohl LLP

(57) ABSTRACT

Methods for forming repeat protein polymers and utilizing the repeat protein polymers to form inorganic structures are provided. The inorganic structures may have features on the nanoscale, and the structures generally do not have the repeat protein polymer incorporated therein.

33 Claims, No Drawings

SYNTHESIS OF INORGANIC STRUCTURES USING TEMPLATION AND CATALYSIS BY SELF ASSEMBLED REPEAT PROTEIN POLYMERS

CROSS REFERENCE TO RELATED APPLICATION

This application claims priority to U.S. Provisional Application No. 60/381,913, filed May 20, 2002.

BACKGROUND OF THE INVENTION

The present invention relates to biomineralization and more specifically, to the formation of inorganic structures using repeat protein polymers as a template and catalyst for the formation.

The formation of highly ordered inorganic materials on a surface has become increasingly important in a variety of fields such as electronics and photonics. The formation of inorganic materials on a nanometer scale is also becoming increasingly desirable as device sizes are reduced. However, the formation of nanometer scale inorganics generally requires extreme conditions such as high pressure, temperature, or pH. Many biological organisms are able to form inorganic materials under ambient conditions in a process known as biomineralization. The structures of inorganic materials formed by biological organisms are highly controlled from the nanometer scale to the macroscopic scale.

For example, the condensation of tetraethoxysilane (TEOS) in a manufacturing setting may require an extreme pH, high temperature, and/or the use of surfactants. Thus, the need remains in the relevant art for a mode of biomineralization that may be utilized to form desired minerals having highly ordered structures at ambient conditions on a commercially viable scale.

SUMMARY OF THE INVENTION

The present invention meets that need by applying recombinant repeat sequence protein polymers to a substrate to act as catalysts and templates for the formation of inorganic structures.

In accordance with an embodiment of the present invention a method of forming an inorganic structure is provided. The method comprises providing a substrate having a repeat protein polymer thereon, the repeat protein polymer having the formula:

$$T_y[(A_n)_x(B)_b(A'_{n'})_{x'}(B')_{b'}(A''_{n''})_{x''}]_i T_{y'}$$

wherein:
T is an amino acid sequence of from about 1 to about 100 amino acids, which may be any sequence comprising fewer than about 20% of the total number of amino acids in the repeat protein copolymer;
y is 0 or 1;
T' and y' are the same as or different from T and y respectively;
A is an individual unit of a repeat amino acid sequence;
n is an integer of at least 2 and not more than 250;
x is 0 or an integer of at least 1 and varies with the number of different amino acids in A so as to provide for at least 30 amino acids in each A repeat sequence;
A', n', and x' are the same as or different from A, n, and x respectively, at least one being different;
A", n", and x" are the same as or different from A, n, and x respectively, at least one being different;
B is any amino acid sequence of about 4 to about 50 amino acids;
B' and b' are the same as or different from B and b respectively; and
i is 1 to 100; and
exposing the substrate to a precursor comprising an inorganic species such that the repeat protein polymer catalyzes the formation of an inorganic structure on the substrate. Additionally, the present invention includes the inorganic structure made by the method.

In accordance with another embodiment of the present invention, a method of forming an inorganic structure is provided. The method comprises providing a first repeat protein polymer having the formula:

$$T_y[(A_n)_x(B)_b(A'_{n'})_{x'}(B')_{b'}(A''_{n''})_{x''}]_i T_{y'}$$

wherein:
T is an amino acid sequence of from about 1 to about 100 amino acids, which may be any sequence comprising fewer than about 20% of the total number of amino acids in the repeat protein copolymer;
y is 0 or 1;
T' and y' are the same as or different from T and y respectively;
A is an individual unit of a repeat amino acid sequence;
n is an integer of at least 2 and not more than 250;
x is 0 or an integer of at least 1 and varies with the number of different amino acids in A so as to provide for at least 30 amino acids in each A repeat sequence;
A', n', and x' are the same as or different from A, n, and x respectively, at least one being different;
A", n", and x" are the same as or different from A, n, and x respectively, at least one being different;
B is any amino acid sequence of about 4 to about 50 amino acids;
B' and b' are the same as or different from B and b respectively; and
i is 1 to 100;
contacting a substrate with the first repeat protein polymer such that the substrate has the first repeat protein polymer thereon; and exposing the substrate having the first repeat protein polymer thereon to a first precursor having an inorganic species such that a first inorganic structure forms on the substrate in areas having the first repeat protein polymer. The method may further comprise providing a second repeat protein polymer in contact with said first inorganic structure, said second repeat protein polymer having the formula:

$$T_y[(A_n)_x(B)_b(A'_{n'})_{x'}(B')_{b'}(A''_{n''})_{x''}]_i T_{y'}$$

wherein:
T is an amino acid sequence of from about 1 to about 100 amino acids, which may be any sequence comprising fewer than about 20% of the total number of amino acids in the repeat protein copolymer;
y is 0 or 1;
T' and y' are the same as or different from T and y respectively;
A is an individual unit of a repeat amino acid sequence;
n is an integer of at least 2 and not more than 250;
x is 0 or an integer of at least 1 and varies with the number of different amino acids in A so as to provide for at least 30 amino acids in each A repeat sequence;

A', n', and x' are the same as or different from A, n, and x respectively, at least one being different;

A", n", and x" are the same as or different from A, n, and x respectively, at least one being different;

B is any amino acid sequence of about 4 to about 50 amino acids;

B' and b' are the same as or different from B and b respectively; and i is 1 to 100; and exposing the second repeat protein polymer to a second precursor comprising an inorganic species such that a second inorganic structure forms on the first inorganic structure.

DETAILED DESCRIPTION OF THE PREFERRED EMBODIMENTS

The present invention utilizes recombinant repeat protein polymers containing repeating units to serve as templates and catalysts for biomineralization. The repeating units may be of natural structure supporting materials such as silk, elastin, and collagen, or the repeating units may be of synthetic structure. For example, the present invention involves synthesizing the repeat protein polymers, placing the repeat protein polymers on a substrate, and exposing the repeat protein polymers to a precursor to form inorganic structures on the substrate.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

The recombinant repeat protein polymers of the present invention are comprised of naturally or non-naturally occurring repeating units. There are more than six hundred repeat protein sequences known to exist in biological systems as of the filing date of this application. Examples include such well known proteins containing repeat amino acid sequences as abductin, elastin, byssus, flagelliform silk, dragline silk, gluten high molecular weight (HMW) subunit, thin, fibronectin, leminin, and collagen. Additionally, synthetic repeating units may be utilized. Individual repeating units may be from 3 to 30 amino acids, and will usually have the same amino acid appearing at least twice in the same unit. For example, individual units of a repeat amino acid sequence may be from about 3 to 8 amino acids. Different unit combinations may be joined together to form a block copolymer or alternating block copolymer. The copolymers may have the following formula:

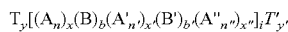

wherein:

T is an amino acid sequence of from about 1 to about 100 amino acids, for example, 1 to 60 amino acids, which may be any sequence, generally being fewer than 20% of the total number of amino acids in the repeat protein copolymer;

y is 0 or 1;

T' and y' are the same as or different from T and y respectively, wherein the analogous symbols have the same definition as their counterparts;

A is an individual unit of a repeat amino acid sequence;

n is an integer of at least 2 and not more than 250;

x is 0 or an integer of at least 1 and will vary with the number of different amino acids in A so as to provide for at least 30 amino acids in each A repeat sequence;

A', n', and x' are the same as or different from A, n, and x respectively, at least one being different, wherein the analogous symbols have the same definition as their counterparts;

A", n", and x" are the same as or different from A, n, and x respectively, at least one being different, wherein the analogous symbols have the same definition as their counterparts;

B is any amino acid sequence of 4 to 50 amino acids, usually being a functional sequence that results in a biological or chemical function or activity;

b is 0 to 3;

B' and b' are the same as or different from B and b respectively, wherein the analogous symbols have the same definition as their counterparts; and i is 1 to 100, for example, 1 to 50 or 1 to 30.

Additionally, the protein polymer may have amino acid sequences that link the repeating A, A', and A" units or amino acid sequences that link between the individual A, A' or A" units. These linking sequences may be from 1 to 10 amino acids and serve to link the repeating units. These repeat polymers can be synthesized by generally recognized methods of chemical synthesis [L Andersson et. al., *Large-scale synthesis of peptides*, Biopolymers 55(3), 227-50 (2000)], genetic manipulation (J. Cappello, Genetically Engineered Protein Polymers, Handbook of Biodegradable Polymers, Domb, A. J.; Kost, J.; Wiseman, D. (Eds.) Harvard Academic Publishers, Amsterdam. Pages 387-414.), and enzymatic synthesis [C. H. Wong & K. T. Wang, *New Developments in Enzymatic Peptide Synthesis*, Experientia 47(11-12), 1123-9 (1991)]. For example, repeat protein polymers useful in the practice of the present invention may be synthesized using the methods described in U.S. Pat. Nos. 5,243,038 and 6,355,776, the disclosures of which are incorporated by reference herein. In another example, a peptide may be synthesized utilizing non-ribosomal peptide synthase (H. V. Dohren, et al., Multifunctional Peptide Synthase, Chem.Rev 97, 2675-2705(1997).

In accordance with an embodiment of the present invention, repeat portions of elastic proteins may be used as the A units. The term "elastic protein" applies to many structural proteins with diverse functions and mechanical properties. Elastic implies the property of elasticity, or the ability to deform reversibly without loss of energy; so elastic proteins should have high resilience. Another meaning for elastic is 'stretchy', or the ability to be deformed to large strains with little force. Thus, elastic proteins may have low stiffness. The combination of high resilience, large strains and low stiffness is characteristic of rubber-like proteins (e.g. resilin and elastin) that function in the storage of elastic-strain energy. Other elastic proteins play very different roles and have very different properties. Collagen fibers provide exceptional energy storage capacity but are not very stretchy. Mussel byssus threads and spider dragline silks are also elastic proteins because, in spite of their considerable strength and stiffness, they are remarkably stretchy. The combination of strength and extensibility, together with low resilience, gives these materials an impressive resistance to fracture (i.e. toughness).

Individual units of particular interest include units found in silk-, elastin-, collagen-, abductin-, byssus-, gluten-, titin-, extensin-, and fibronectin-like proteins. Silk-like proteins have a repeating unit of SGAGAG (G=glycine; A=alanine; S=serine) (SEQ ID NO: 1). This repeating unit is found in naturally occurring silk fibroin protein, which can be represented as GAGAG(SGAGAG)$_8$SGAAGY (Y=tyrosine) (SEQ ID NO: 2). Elastin-like proteins have a base repeating unit of GVGVP (V=valine; P=proline) (SEQ ID NO:3). This repeating unit may be found in naturally occurring elastin. Collagen-like proteins have repeating units of G-x-y (x=any amino acid, often alanine or proline; y=any amino acid, often proline or hydroxy-proline). Abductin-like proteins have a base repeating unit of GGFGGMGGGx (F=phenylalanine; M=methionine) (SEQ ID NO: 4). Byssus-like proteins have a repeating unit of (GPGGG) (SEQ ID NO: 5). Gluten-like proteins of the high molecular weight subunit have repeating units of PGQGQQ (SEQ ID NO: 6), GYYPTSPQQ (SEQ ID NO: 7), and GQQ (Q=glutamine; Y=tyrosine; T=threonine) (SEQ ID NO: 8). Titin-like proteins have a repeating units of PPAKVPEVPKKPVPEEKVPVPVPKKPEA (K=Lysine, E=Glutamic Acid) (SEQ ID NO: 9) and are found in the heart, psoas, and soleus muscle. Extensin-like proteins have repeating units of SPPPPSPKYVYK (SEQ ID NO: 10). Fibronectin-like proteins have repeating units of RGDS (R=arginine; D=aspartic acid) (SEQ ID NO: 11).

Additional repeating units of interest are found in gliadin, glue polypolypeptide, ice nucleating protein, keratin, mucin, RNA polymerase II, and resilin. Gliadin has a repeating unit of PQQPY (SEQ ID NO: 12). The glue polypeptide has a repeating unit of PTTTK (SEQ ID NO: 13). The ice nucleating protein has a repeating unit of AGYGSTGT (SEQ ID NO: 14). Keratin has repeating units of YGGSSGGG (SEQ ID NO: 15) or FGGGS (SEQ ID NO: 16). Mucin has a repeating unit of TTTPDV (SEQ ID NO: 17). RNA polymerase II has a repeating unit of YSPTSPS (SEQ ID NO: 18). Additionally, resilin, a rubber-like protein contains repeating units.

Copolymers utilizing these natural repeating units may have their properties altered by appropriate choice of different units, the number of units in each multimer, the spacing between units, and the number of repeats of the multimer combination assembly. The spacing between units refers to the amino acid sequences represented by B or B' in the above formula. For example, the copolymers may be combinations of silk units and elastin units to provide silk-elastin copolymers having properties distinctive from polymers having only the same monomeric unit. In a further example, silk-elastin repeat protein polymers may have their solubility decreased as the number or silk units (SEQ ID NO: 1) is increased. Additionally, altering the spacing, B, between individual repeat units, A, may affect the rate of precipitation of an inorganic precursor as discussed herein.

In accordance with an embodiment of the present invention, the repeat protein polymers may have an overall cationic charge, and the overall cationic charge may enhance the ability of the repeat protein polymer to catalyze the formation of inorganic structures as discussed hereafter. Overall cationic charge shall be understood as referring to the net cationic (+) charge present after the summation of individual amino acid residue charges at a given pH and temperature. For example, the pH may be 7 and the temperature may be 20° C. In accordance with another embodiment of the present invention, the repeat protein polymers may have silk units (SEQ ID NO: 1) and/or collagen like units, and repeat protein polymers having these units may have their ability to catalyze the formation of inorganic structures enhanced. In accordance with another embodiment of the present invention, the repeat protein polymers may have at least one or a plurality of lysine residues.

In accordance with an embodiment of the present invention, the repeat portion of the repeat protein polymers, $[(A_n)_x(B)_b(A'_{n'})_x(B')_b(A''_{n''})_{x''}]_i$, may be: head-[(GAGAGS)$_2$ (GVGVP)$_3$GKGVP (GVGP)$_4$(GAGAGS)$_2$]$_{13}$-tail (SEQ ID NO: 19); head-[(GVGVP)$_4$GEGVP (GVGVP)$_3$(GAGAGS)$_4$]-tail (SEQ ID NO: 20); head-[(GAGAGS)$_3$(GVGVP)$_3$GKGVP(GVGVP)$_4$]$_{12}$-tail (SEQ ID NO 21); head-[(GAHGPAGPK)$_2$(GAQGPAGPG)$_{24}$ (GAHGPAGPK)$_2$]$_4$-tail (SEQ ID NO: 22); head-[(GVGVP)$_4$ GKGVP(GVGVP)$_3$(GAGAGS)$_3$]$_{12}$-tail (SEQ ID NO: 23); head-[(GAPGTPGPQGLPGSP)$_4$]$_{13}$-tail (SEQ ID NO: 24); and head-[(GAPGAPGSQGAPGLQ)$_4$]$_{13}$-tail (SEQ ID NO: 25). The head and tail portions of the repeat sequences correspond to T and T' and may be any suitable sequence. For example, the head and tail sequences may signal the start and stop for the repeat protein polymer. Suitable head sequences include, but are not limited to, MDPVVLQRRDWENPGVTQLNRLAAHPPFASDPM (SEQ ID NO: 26). Suitable tail sequences include, but are not limited to, GAGAMDPGRYQDLRSHHHHHH (SEQ ID NO: 27), MDPGRYQDLRSHHHHHH (SEQ ID NO: 28), MDPGRYGLSAGRYHYQLVWCQK (SEQ ID NO: 29), MDPTRYGLSAGRYHYQLVWCQK (SEQ ID NO: 30), MDPGRYQLSAGRYHYQLVWCQK (SEQ ID NO: 31), MDPTRYQLSAGRYHYQLVWCQK (SEQ ID NO: 32), GAGAMDPGRYQDLRSHHHHHH (SEQ ID NO: 33), and MDPGRYGDLRSHHHHHH (SEQ ID NO: 34).

Once the repeat protein polymer has been synthesized and purified as needed, the repeat protein polymer or a plurality of repeat protein polymers are generally applied to a substrate or a substrate is contacted with the repeat protein polymers. The repeat protein polymers may be the different or the same. For example, one, two, or three of the repeat protein polymers may be different. The substrate may be any suitable surface such as steel, glass, silicon, mica, graphite, plastic, teflon or the like. While not wishing to be bound by theory, it is believed that once applied to the substrate, many of the repeat protein polymers may exhibit desirable surface properties due to beta sheet structures and the ability to form self-assembled monolayers (SAM's). SAM's are formed by the spontaneous aggregation and organization of the protein into a monolayer. The SAM may be in the form of a patterned deposition due to the use of repeat sequences. The SAM is at or near thermodynamic equilibrium, and therefore the SAM tends to reject defects. The presence of SAMs may be confirmed using atomic force microscopy or scanning electron microscopy.

The repeat protein may be applied to a substrate using a variety of techniques. For example, the protein may be spin coated on the substrate. However, it may be desirable to form an ordered and patterned structure on the substrate. Therefore, techniques such as soft lithography, rapid printing or photolithography may be utilized to form a pattern of protein on a substrate. For example, soft lithography or rapid printing can be utilized to form the pattern.

Soft lithography is a non-photolithographic technique useful for carrying out micro- and nanofabrication. Soft lithography may produce patterns and structures having feature sizes ranging from about 30 nm to about 100 μm. Soft lithography generally utilizes an elastomeric stamp or mold (soft lithographic stamp) with patterned relief structures on its surface used to generate the desired pattern. In one embodiment, an elastomeric stamp may be formed using a master mold. The stamp is "inked" with the repeat protein polymer in a solution and a substrate is contacted with the stamp. A pattern of SAM protein is formed on the substrate in the areas where the relief structures of the stamp contacted the substrate. Examples of suitable soft lithographic stamps are found in published U.S. patent application Ser. Nos. 20010027570 and 20010013294, the disclosures of which are incorporated by reference herein. Alternatively, a mold may be formed and placed in contact with a substrate. A protein solution is then placed at one end of the mold, and channels in the mold fill by capillary action to form a pattern after the mold is removed. Additionally, the substrate itself may be patterned by soft lithography, and the protein may then be applied to the substrate to fill the pattern. For example, placing a mold on the substrate and filling it with a prepolymer may pattern the substrate. U.S. Pat. No. 6,368,877 discloses several methods of forming patterned SAMs using soft lithography and is incorporated by reference herein.

In rapid printing, a self assembling "ink" comprising the protein in solution is used with rapid printing procedures to form patterned structures in a very short period of time. Suitable rapid printing procedures include pen lithography, ink-jet printing, and dip-coating. The rapid printing procedures use the ink to form a desired pattern on suitable substrates. The ink thus forms patterned SAMs that define functional, hierarchically organized structures in seconds. Suitable rapid printing techniques and apparatus are described in Hongyou Fan, *Rapid Prototyping of Patterned Functional Nanostructures*, Nature 405, 56-60 (2000), which is incorporated by reference herein.

Once the repeat protein polymer has been placed on or applied to the substrate or the substrate has been contacted with the repeat protein polymer, the substrate is exposed to a precursor containing a desired inorganic species, and the repeat protein polymer catalyzes the formation of an inorganic structure on the substrate. For purposes of defining and describing the present invention, the terms "formation", "formed", and "forms" shall be understood as referring the deposition of an inorganic structure on a substrate. The repeat protein polymer on the surface of the substrate acts both as a catalyst and a template in the formation of a desired inorganic structure from the precursor. The inorganic structures are generally formed only in areas of the substrate having at least one repeat protein polymer. For example, the polymer may be exposed to a silicon containing precursor to cause the formation of silica on the substrate. Examples of silicon containing precursors include, but are not limited to, tetraethoxysilane solutions (TEOS), TEOS dissolved in an acid to make a silicic acid solution, 3-aminopropyltriethoxysilane, and phenyltriethoxysilane. The repeat protein polymer acts as a catalyst in the reaction, and therefore does not form a silica-protein composite material. Additionally, the repeat protein polymer acts as a template for the formation of the silica because silica formation will occur only in areas that contain the repeat protein polymer. Thus, a silica structure may be formed that conforms to the pattern formed on the surface by the repeat protein polymer. Alternatively, the precursor may contain other inorganic species. For example, the precursors may contain zirconium, silver, copper, cadmium, tantalum, yttrium, iron, titanium, cobalt or calcium species to form their respective metal, salt, and minerals or possible combinations of hybrid structures on the substrate. For example, suitable precursors include, but are not limited to, yttriumethoxide, silver nitrate, and calcium chloride. In one embodiment, the inorganic structures may have features on the order of about 1 to about 999, about 1 to about 250, or about 1 to about 100 nanometers. It will be understood that a plurality of precursors may be used in the present invention, and it will be further understood that the plurality of precursors may be the same or different precursors. Thus, a product comprising nanopatterned structures may be formed by the methods of the present invention.

For example, self-assembling nanometer-sized aggregates of mesoporous fibrous silica particles may be formed when a hydrolyzed TEOS solution is used in conjunction with repeat protein polymers of the present invention. Mesoporous fibrous silica may refer to porous material having wall portions defining meso-porous sized channels having a mean diameter of between about 15 Angstrom to about 100 Angstrom and a narrow diameter distribution of approx~<30 Angstrom, the silica material having a void volume from said meso-pore sized channels of approximately~>0.1 cm3/g (Philos Trans R Soc Lond B Biol Sci Feb. 28, 2002; 357(1418):121-32). These silica particles may be in the form of fibrous silica with the fibers being on the nanometer scale in size. Mesoporous fibrous silica particles may be used in a variety of applications. For example, the particles may be used for catalysis, memory storage, replication, heat reflecting materials, thermal insulators, and optical reflectors.

The inorganic structure may be formed under ambient conditions, such as room temperature and atmospheric pressure, which is particularly advantageous when the substrate cannot be exposed to high temperatures or pressures. After the formation of the inorganic structure, subsequent layers of repeat protein polymer and inorganic material may be formed in accordance with the above processes. In this manner, stacked three-dimensional structures may be formed. Thus, the inorganic structures formed by the methods of the present invention may be used in a variety of applications such as electronics, photonics, and nanocomposite materials.

In order that the invention may be more readily understood, reference is made to the following examples, which are intended to be illustrative of the invention, but are not intended to be limiting in scope.

EXAMPLE 1

A genetically engineered silk-elastin copolymer SELP47K (SEQ ID NO: 19) was isolated and purified from *E. coli* bacteria. The *E. coli* containing the SELP47K (SEQ ID NO: 19) recombinant DNA was obtained from Protein Polymer Technologies, Inc. of San Diego, Calif. The SELP47K (SEQ ID NO: 19) had a general structure of:

```
head-[(GAGAGS)_2(GVGVP)_3GKGVP      (SEQ ID NO: 19)
(GVGP)_4(GAGAGS)_2]_13-tail.
```

The copolymer contained 780 amino acids in the repeating unit.

Bovine albumin serum (BSA) was purchased from Sigma Aldrich, St. Louis, Mo. A 13% solution of SELP47K (SEQ ID NO: 19) in water was prepared. A 13% solution of BSA in water was prepared. A stainless steel coupon was spin coated with the SELP47K (SEQ ID NO: 19) solution to a thickness of 2 µm to form a SELP47K (SEQ ID NO: 19) protein film. A stainless steel coupon was spin coated with the BSA solution to a thickness of 2 µm to form a BSA protein film.

A hydrolyzed TEOS solution was made using 1M TEOS dissolved in 1 mM HCl overnight. 100 µl of the TEOS solution was filtered and mixed with 900 µl of Tris buffer, pH 8.0, to prepare the assay solution. The TEOS assay solution was placed on the film of both the SELP47K (SEQ ID NO: 19) and BSA and in a corner of both steel coupons where no protein film was present.

It was observed that silica precipitation completed within one minute on the SELP47K (SEQ ID NO: 19) film. No silica precipitation was observed on the BSA film. Additionally, no silica precipitation was observed on the uncoated corners of the steel coupons. The SELP47K (SEQ ID NO: 19) film was analyzed to confirm the silica precipitation by removing the white solid precipitated over the SELP47K (SEQ ID NO: 19) film mechanically and dissolving the precipitated silica in NaOH and reacting the solution with molybdic acid to observe the color.

EXAMPLE 2

A 10-20% solution of the SELP47K (SEQ ID NO: 19) obtained in Example 1 in water was prepared. A stainless steel coupon was spin coated with the SELP47K (SEQ ID NO: 19) solution to a thickness of 2 μm to form a SELP47K (SEQ ID NO: 19) protein film. A yttrium ethoxide solution was placed on the film of the SELP47K (SEQ ID NO: 19). Ytrrbia precipitation was observed immediately on the protein polymer film whereas no such precipitation was seen when dropped directly on the metal coupon having no SELP47K (SEQ ID NO: 19) protein polymer film.

EXAMPLE 3

A SELP37K (SEQ ID NO: 21) copolymer having a structure of: head-[(GAGAGS)$_3$(GVGVP)$_3$GKGVP (GVGVP)$_4$]$_{12}$-tail (SEQ ID NO 21) may be obtained from *E. coli* bacteria containing recombinant DNA. The *E. coli* may be prepared in accordance with the methods described un U.S. Pat. Nos. 5,243,038 and 6,355,776.

A 10-20% solution of SELP37K (SEQ ID NO: 21) in water was prepared. A stainless steel coupon was spin coated with the SELP37K (SEQ ID NO: 21) solution to a thickness of 2 μm to form a SELP37K (SEQ ID NO: 21) protein film. A hydrolyzed TEOS solution was made using 1M TEOS dissolved in 1 mM HCl overnight. 100 μl of the hydrolyzed TEOS solution was filtered and mixed with 900 μl of Tris buffer, pH 8.0, to prepare the assay solution. A drop of TEOS assay solution was placed on the film of the SELP37K (SEQ ID NO: 21). Silica precipitation was observed. It was observed that within five minutes silica precipitation completed on the SELP37K (SEQ ID NO: 21) film. No silica precipitation was observed on the control BSA film. Additionally, no silica precipitation was observed on the uncoated corners of the steel coupons. The SELP37K (SEQ ID NO: 21) film was further analyzed to confirm the silica precipitation by removing the white solid precipitated over the SELP37K (SEQ ID NO: 21) film mechanically and dissolving the precipitated silica in NaOH and reacting the solution with molybdic acid to observe the color.

EXAMPLE 4

A collagen like protein copolymer DCP6 (SEQ ID NO: 22) having a general structure of

```
                                              (SEQ ID NO: 22)
head-[(GAHGPAGPK)_2(GAQGPAGPG)_24(GAHGPAGPK)_2]_4-tail
``` was obtained from *E. Coli* bacteria containing recombinant DNA. The *E. Coli* was prepared in accordance with the methods described un U.S. Pat. Nos. 5,243,038 and 6,355,776.

A 10-20% solution of DCP6 copolymer (SEQ ID NO: 22) in water was prepared. A stainless steel coupon was spin coated with the copolymer solution to a thickness of 2 μm to form a collagen like protein film. A hydrolyzed TEOS solution was made using 1M TEOS dissolved in 1 mM HCl overnight. 100 μl of the TEOS solution was filtered and mixed with 900 μl of Tris buffer, pH 8.0, to prepare the assay solution. The hydrolyzed TEOS assay solution was placed on the film of the copolymer. Silica precipitation was observed within a few minutes.

EXAMPLE 5

A collagen like protein copolymer CLP3.7 (SEQ ID NO: 24) having a general structure of:

```
head-[(GAPGTPGPQGLPGSP)_4]_13-tail      (SEQ ID NO: 24)
``` was obtained from *E. Coli* bacteria containing recombinant DNA. The *E. Coli* was prepared in accordance with the methods described un U.S. Pat. Nos. 5,243,038 and 6,355,776. The CLP3.7 copolymer has a molecular weight of 72,637.

A 10-20% solution of CLP3.7 copolymer (SEQ ID NO: 24) in water was prepared. A stainless steel coupon was spin coated with the copolymer solution to a thickness of 2 μm to form a collagen like protein film. A hydrolyzed TEOS solution was made using 1M TEOS dissolved in 1 mM HCl overnight. 100 μl of the TEOS solution was filtered and mixed with 900 μl of Tris buffer, pH 8.0, to prepare the assay solution. The hydrolyzedTEOS assay solution was placed on the film of this copolymer. Silica precipitation was observed slowly and was completed within several minutes.

PROPHETIC EXAMPLE 6

A SELP copolymer (SEQ ID NO: 20) having a general structure of:

```
                                          (SEQ ID NO: 20)
head-[(GVGVP)_4GEGVP(GVGVP)_3(GAGAGS)_4]-tail
``` may be obtained from *E. coli* bacteria containing recombinant DNA. The *E. coli* may be prepared in accordance with the methods described in U.S. Pat. Nos. 5,243,038 and 6,355,776. The copolymer will contain 64 amino acids.

A 10-20% solution of SELP (SEQ ID NO: 20) in water can be prepared. A stainless steel coupon may be spin coated with the SELP (SEQ ID NO: 20) solution to a thickness of 2 μm to form a SELP (SEQ ID NO: 20) protein film. A hydrolyzed TEOS solution may be made using 1M TEOS dissolved in 1 mM HCl overnight. 100 μl of the hydrolyzed TEOS solution can be filtered and mixed with 900 μl of Tris buffer, pH 8.0, to prepare the assay solution. The TEOS assay solution may be placed on the film of the SELP (SEQ ID NO: 20). Silica precipitation should be observed.

PROPHETIC EXAMPLE 7

A SELP copolymer (SEQ ID NO: 23) having a general structure of

```
                                          (SEQ ID NO: 23)
head-[(GVGVP)_4GKGVP(GVGVP)_3(GAGAGS)_3]_12-tail
``` may be obtained from *E. Coli* bacteria containing recombinant DNA. The *E. Coli* may be prepared in accordance with the methods described un U.S. Pat. Nos. 5,243,038 and 6,355,776.

A 10-20% solution of SELP (SEQ ID NO: 23) in water can be prepared. A stainless steel coupon may be spin coated with the SELP (SEQ ID NO: 23) solution to a thickness of 2 μm to form a SELP (SEQ ID NO: 23) protein film. A TEOS solution may be made using 1M TEOS dissolved in 1 mM HCl overnight. 100 μl of the TEOS solution can be filtered and mixed with 900 μl of Tris buffer, pH 8.0, to prepare the assay solution. The TEOS assay solution may be placed on the film of the SELP (SEQ ID NO: 23). Silica precipitation should be observed.

PROPHETIC EXAMPLE 8

A collagen like protein copolymer (SEQ ID NO: 25) having a general structure of

```
head-[(GAPGAPGSQGAPGLQ)4]13-tail    (SEQ ID NO: 25)
``` may be obtained from *E. Coli* bacteria containing recombinant DNA. The *E. Coli* may be prepared in accordance with the methods described in U.S. Pat. Nos. 5,243,038 and 6,355,776.

A 10-20% solution of copolymer (SEQ ID NO: 25) in water can be prepared. A stainless steel coupon may be spin coated with the copolymer (SEQ ID NO: 25) solution to a thickness of 2 μm to form a protein film. A TEOS solution may be made using 1M TEOS dissolved in 1 mM HCl overnight. 100 μl of the TEOS solution can be filtered and mixed with 900 μl of Tris buffer, pH 8.0, to prepare the assay solution. The TEOS assay solution may be placed on the film of the copolymer(SEQ ID NO: 25). Silica precipitation should be observed.

PROPHETIC EXAMPLE 9

A $CaCO_3$ inorganic structure may be formed using SELP47K (SEQ ID NO: 19). The SELP47K (SEQ ID NO: 19) will be dissolved in 1 ml of 7.5 mM $CaCl_2$ solution and this 1 ml SELP47K (SEQ ID NO: 19) solution in $CaCl_2$ will be placed into a well containing a cover-slip and the whole set up will be covered with aluminum foil with a few pin holes on top of the well. $CaCO_3$ crystals will be formed inside a closed desiccator for two days by slow diffusion of gases released by the decomposition of ammonium bicarbonate placed at the bottom of desiccator. After 2 days the cover-slip will be lifted carefully from the well, rinsed gently with deionized water, air dried at room temperature and will be used for characterization.

What is claimed is:

1. A method of forming an inorganic structure, comprising:
providing a substrate having a repeat protein polymer thereon, said repeat protein polymer having the formula:

$$T_y[(A)_x(B)_b(A')_{x'}(B')_b(A'')_{x''}]_i T'_{y'}$$

wherein:
T and T' are amino acid sequences of from about 1 to about 100 amino acids, which may be any sequence comprising fewer than about 20% of the total number of amino acids in the repeat protein polymer,
y and y' are 0 or 1;
T' and y' are the same as or different from T and y respectively;
A, A', and A'' are individual units of a repeat amino acid sequence selected from SGAGAG (G=glycine; A=alanine; S=serine)(SEQ ID NO: 1), GVGVP (V=valine; P=proline)(SEQ ID NO: 3), GGFGGMGGGx (F=phenylalanine; M=methionine)(SEQ ID NO: 4), (GPGGG)(SEQ ID NO: 5), PGQGQQ (SEQ ID NO: 6), GYYPTSPQQ (SEQ ID NO: 7), GQQ (Q=glutamine; Y=tyrosine; T=threonine)(SEQ ID NO: 8), PPAKVPEVPKKPVPEEKVPVPVPKK-PEA (K=Lysine, E=Glutamic Acid) (SEQ ID NO: 9), SPPPPSPKYVYK (SEQ ID NO: 10), and RGDS (R=arginine; D=aspartic acid)(SEQ ID NO: 11), PQQPY (SEQ ID NO: 12), PTTTK (SEQ ID NO: 13), AGYGSTGT (SEQ ID NO: 14), YGGSSGGG (SEQ ID NO: 15), FGGGS (SEQ ID NO: 16), TTTPDV (SEQ ID NO: 17), YSPTSPS (SEQ ID NO: 18), and combinations thereof
where x, x', and x'' are integers of at least 1 which vary with the number of different amino acids in A, A', and A'' so as to provide for at least 30 amino acids in each A, A', and A'' repeat sequence;
where A', and x' are the same as or different from A, and x respectively, at least one being different;
where A'', and x'' are the same as or different from A, and x respectively, at least one being different;
B and B' are any amino acid sequences of about 4 to about 50 amino acids;
b and b' are 0 to 3;
B' and b' are the same as or different from B and b respectively; and
i is 1 to 100; and
exposing said substrate to a precursor comprising an inorganic species, wherein said inorganic species is selected from the group consisting of silicon, zirconium, silver, copper, cadmium, tantalum, yttrium, iron, titanium, cobalt, calcium, and combinations thereof, such that said repeat protein polymer catalyzes the formation of an inorganic structure on said substrate.

2. The method as claimed in claim 1 wherein said substrate has a plurality of said repeat protein polymers thereon.

3. The method as claimed in claim 2 wherein each of said plurality of repeat protein polymers are the same.

4. The method as claimed in claim 2 wherein at least one of said plurality of repeat protein polymers is different from another at least one of said plurality of repeat protein polymers.

5. The method as claimed in claim 1 wherein T and T' are amino acid sequences of from about 1 to about 60 amino acids.

6. The method as claimed in claim 1 wherein i is 1 to 50.

7. The method as claimed in claim 1 wherein i is 1 to 30.

8. The method as claimed in claim 1 wherein said inorganic species comprises a species having silicon.

9. The method as claimed in claim 1 wherein said inorganic structure forms on the surface of said substrate in areas having said repeat protein polymer.

10. The method as claimed in claim 1 wherein said substrate has a surface, and wherein said repeat protein polymer forms a pattern on said surface.

11. The method as claimed in claim 10 wherein said inorganic structure forms on said substrate in areas having said repeat protein polymer.

12. The method as claimed in claim 1 wherein said inorganic structure has a length of from about 1 to about 999 nanometers.

13. The method as claimed in claim 1 further comprising placing said repeat protein polymer on said substrate with a soft lithographic stamp.

14. The method as claimed in claim 1 further comprising placing said repeat protein polymer on said substrate by rapid printing.

15. The method as claimed in claim 1 wherein said repeat protein polymer comprises a self assembled monolayer on said substrate.

16. The method as claimed in claim 1 wherein said inorganic structure comprises mesoporous fibrous silica particles.

17. The method as claimed in claim 1 wherein said repeat protein polymer has an overall cationic charge.

18. The method as claimed in claim 1 wherein said repeat protein polymer has at least one lysine.

19. A method of forming an inorganic structure, comprising:

providing a substrate having a repeat protein polymer thereon, said repeat protein polymer being selected from the group consisting of:

head-[(GAGAGS)$_2$(GVGVP)$_3$GKGVP(GVGP)$_4$(GAGAGS)$_2$]$_{13}$-tail,  (SEQ ID NO: 19)

head-[(GVGVP)$_4$GEGVP(GVGVP)$_3$(GAGAGS)$_4$]-tail,  (SEQ ID NO: 20)

head-[(GAGAGS)$_3$(GVGVP)$_3$GKGVP(GVGVP)$_4$]$_{12}$-tail,  (SEQ ID NO 21)

head-[(GAHGPAGPK)$_2$(GAQGPAGPG)$_{24}$(GAHGPAGPK)$_2$]$_4$-tail,  (SEQ ID NO: 22)

head-[(GVGVP)$_4$GKGVP(GVGVP)$_3$(GAGAGS)$_3$]$_{12}$-tail,  (SEQ ID NO: 23)

head-[(GAPGTPGPQGLPGSP)$_4$]$_{13}$-tail,  (SEQ ID NO: 24)

head-[(GAPGAPGSQGAPGLQ)$_4$]$_{13}$-tail,  (SEQ ID NO: 25)

and mixtures thereof, and exposing said substrate to a precursor comprising an inorganic species, wherein said inorganic species is selected from the group consisting of silicon, zirconium, silver, copper, cadmium, tantalum, yttrium, iron, titanium, cobalt, calcium, and combinations thereof, such that said repeat protein polymer catalyzes the formation of an inorganic structure on said substrate.

20. A method of forming an inorganic structure, comprising:

providing a first repeat protein polymer having the formula:

$$T_y[(A)_x(B)_b(A')_{x'}(B')_{b'}(A'')_{x''}]_iT_{y'}'$$

wherein:

T and T' are amino acid sequence of from about 1 to about 100 amino acids, which may be any sequence comprising fewer than about 20% of the total number of amino acids in the repeat protein polymer, y and y' are 0 or 1;

T' and y' are the same as or different from T and y respectively;

A, A', and A'' are individual units of a repeat amino acid sequence selected from SGAGAG (G=glycine; A=alanine; S=serine)(SEQ ID NO: 1), GVGVP (V=valine; P=proline)(SEQ ID NO: 3), GGFG-GMGGGx (F=phenylalanine; M=methionine)(SEQ ID NO: 4), (GPGGG)(SEQ ID NO: 5), PGQGQQ (SEQ ID NO: 6), GYYPTSPQQ (SEQ ID NO: 7), GQQ (Q=glutamine; Y=tyrosine; T=threonine)(SEQ ID NO: 8), PPAKVPEVPKKPVPEEKVPVPVPKK-PEA (K=Lysine, E=Glutamic Acid) (SEQ ID NO: 9), SPPPPSPKYVYK (SEQ ID NO: 10), and RGDS (R=arginine; D=aspartic acid)(SEQ ID NO: 11), PQQPY (SEQ ID NO: 12), PTTTK (SEQ ID NO: 13), AGYGSTGT (SEQ ID NO: 14), YGGSSGGG (SEQ ID NO: 15), FGGGS (SEQ ID NO: 16), TTTPDV (SEQ ID NO: 17), YSPTSPS (SEQ ID NO: 18), and combinations thereof where x, x', and x'' are integers of at least 1 which vary with the number of different amino acids in A, A', and A'' so as to provide for at least 30 amino acids in each A, A', and A'' repeat sequence;

where A', and x' are the same as or different from A, and x respectively, at least one being different;

where A'', and x'' are the same as or different from A, and x respectively, at least one being different;

B and B' are any amino acid sequences of about 4 to about 50 amino acids;

b and b' are 0 to 3;

B' and b' are the same as or different from B and b respectively; and i is 1 to 100; and contacting a substrate with said first repeat protein polymer such that said substrate has said first repeat protein polymer thereon; and exposing said substrate having said first repeat protein polymer thereon to a first precursor having an inorganic species, wherein the inorganic species is selected from the group consisting of silicon, zirconium, silver, copper, cadmium, tantalum, yttrium, iron, titanium, cobalt, calcium, and combinations thereof, such that a first inorganic structure forms on said substrate in areas having said first repeat protein polymer.

21. The method as claimed in claim 20 further comprising:

providing a second repeat protein polymer in contact with said first inorganic structure, said second repeat protein polymer having the formula:

$$T_y[(A)_x(B)_b(A')_{x'}(B')_{b'}(A'')_{x''}]_iT_{y'}'$$

wherein:

T and T' are amino acid sequence of from about 1 to about 100 amino acids, which may be any sequence comprising fewer than about 20% of the total number of amino acids in the repeat protein polymer, y and y' are 0 or 1;

T' and y' are the same as or different from T and y respectively;

A, A', and A" are individual units of a repeat amino acid sequence selected from SGAGAG (G=glycine; A=alanine; S=serine)(SEQ ID NO: 1), GVGVP (V=valine; P=proline)(SEQ ID NO: 3), GGFG-GMGGGx (F=phenylalanine; M=methionine)(SEQ ID NO: 4), (GPGGG)(SEQ ID NO: 5), PGQGQQ (SEQ ID NO: 6), GYYPTSPQQ (SEQ ID NO: 7), GQQ (Q=glutamine; Y=tyrosine; T=threonine)(SEQ ID NO: 8), PPAKVPEVPKKPVPEEKVPVPVPKK-PEA (K=Lysine, E=Glutamic Acid) (SEQ ID NO: 9), SPPPPSPKYVYK (SEQ ID NO: 10), and RGDS (R=arginine; D=aspartic acid)(SEQ ID NO: 11), PQQPY (SEQ ID NO: 12), PTTTK (SEQ ID NO: 13), AGYGSTGT (SEQ ID NO: 14), YGGSSGGG (SEQ ID NO: 15), FGGGS (SEQ ID NO: 16), TTTPDV (SEQ ID NO: 17), YSPTSPS (SEQ ID NO: 18), and combinations thereof where x, x', and x" are integers of at least 1 which vary with the number of different amino acids in A, A', and A" so as to provide for at least 30 amino acids in each A, A', and A" repeat sequence;

where A', and x' are the same as or different from A, and x respectively, at least one being different;

where A", and x" are the same as or different from A, and x respectively, at least one being different;

B and B' are any amino acid sequences of about 4 to about 50 amino acids;

b and b' are 0 to 3;

B' and b' are the same as or different from B and b respectively; and i is 1 to 100; and exposing said second repeat protein polymer to a second precursor comprising an inorganic species, wherein said inorganic species is selected from the group consisting of silicon, zirconium, silver, copper, cadmium, tantalum, yttrium, iron, titanium, cobalt, calcium, and combinations thereof, such that a second inorganic structure forms on said first inorganic structure.

22. The method as claimed in claim 20 wherein said first inorganic structure and said second inorganic structure comprise a single inorganic structure.

23. The method as claimed in claim 22 wherein said single inorganic structure comprises a three-dimensional structure.

24. The method as claimed in claim 21 wherein said first repeat protein polymer and said second repeat protein polymer are the same.

25. The method as claimed in claim 21 wherein said first repeat protein polymer and said second repeat protein polymer are different.

26. The method as claimed in claim 21 wherein said first precursor and said second precursor are the same.

27. The method as claimed in claim 21 wherein said first precursor and said second precursor are different.

28. The method as claimed in claim 1 wherein the precursor is selected from the group consisting of TEOS, TEOS dissolved in acid, 3-aminopropyltriethoxysilane, phenyltriethoxysilane, yttriumethoxide, silver nitrate, calcium chloride, and combinations thereof.

29. The method as claimed in claim 28 wherein the precursor is selected from the group consisting of TEOS dissolved in acid, yttriumethoxide, calcium chloride, and combinations thereof.

30. The method as claimed in claim 19 wherein the precursor is selected from the group consisting of TEOS, TESO dissolved in acid, 3-aminopropyltriethoxysilane, phenyltriethoxysilane, yttriumethoxide, silver nitrate, calcium chloride, and combinations thereof.

31. The method as claimed in claim 30 wherein the precursor is selected from the group consisting of TEOS dissolved in acid, yttriumethoxide, calcium chloride, and combinations thereof.

32. The method as claimed in claim 20 wherein the precursor is selected from the group consisting of TEOS, TEOS dissolved in acid, 3-aminopropyltriethoxysilane, phenyltriethoxysilane, yttriumethoxide, silver nitrate, calcium chloride, and combinations thereof.

33. The method as claimed in claim 32 wherein the precursor is selected from the group consisting of TEOS dissolved in acid, yttriumethoxide, calcium chloride, and combinations thereof.

* * * * *

SEQUENCE LISTING

```
<160> NUMBER OF SEQ ID NOS: 34

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 1

Ser Gly Ala Gly Ala Gly
 1               5

<210> SEQ ID NO 2
<211> LENGTH: 59
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ala Gly Ala Gly Ser Gly Ala Gly Ala Gly Ser Gly Ala Gly Ala
 1               5                  10                  15

Gly Ser Gly Ala Gly Ala Gly Ser Gly Ala Gly Ala Gly Ser Gly Ala
             20                  25                  30

Gly Ala Gly Ser Gly Ala Gly Ala Gly Ser Gly Ala Gly Ala Gly Ser
         35                  40                  45

Gly Ala Gly Ala Gly Ser Gly Ala Ala Gly Tyr
     50                  55

<210> SEQ ID NO 3
```

-continued

```
<211> LENGTH: 5
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 3

Gly Val Gly Val Pro
 1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence:
      Illustrative peptide
<220> FEATURE:
<221> NAME/KEY: MOD_RES
<222> LOCATION: (10)
<223> OTHER INFORMATION: Any amino acid, often, Ala or Pro

<400> SEQUENCE: 4

Gly Gly Phe Gly Gly Met Gly Gly Gly Xaa
 1               5                  10

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 5

Gly Pro Gly Gly Gly
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 6

Pro Gly Gln Gly Gln Gln
 1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 7

Gly Tyr Tyr Pro Thr Ser Pro Gln Gln
 1               5

<210> SEQ ID NO 8
<211> LENGTH: 3
<212> TYPE: PRT
<213> ORGANISM: Artificial Sequence
<220> FEATURE:
<223> OTHER INFORMATION: Description of Artificial Sequence:
```

Illustrative peptide

<400> SEQUENCE: 8

Gly Gln Gln
1

<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 9

Pro Pro Ala Lys Val Pro Glu Val Pro Lys Lys Pro Val Pro Glu Glu
1               5                   10                  15

Lys Val Pro Val Pro Val Pro Lys Lys Pro Glu Ala
            20                  25

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 10

Ser Pro Pro Pro Pro Ser Pro Lys Tyr Val Tyr Lys
1               5                   10

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 11

Arg Gly Asp Ser
1

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 12

Pro Gln Gln Pro Tyr
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 13

Pro Thr Thr Thr Lys
1               5

```
<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 14

Ala Gly Tyr Gly Ser Thr Gly Thr
 1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 15

Tyr Gly Gly Ser Ser Gly Gly Gly
 1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 16

Phe Gly Gly Gly Ser
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 17

Thr Thr Thr Pro Asp Val
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:
      Synthetic polymer

<400> SEQUENCE: 18

Tyr Ser Pro Thr Ser Pro Ser
 1               5

<210> SEQ ID NO 19
<211> LENGTH: 780
<212> TYPE: PRT
<213> ORGANISM: Artificial Sequence
<220> FEATURE:
<223> OTHER INFORMATION: Description of Artificial Sequence: Synthetic
      polymer
```

<400> SEQUENCE: 19

```
Gly Ala Gly Ala Gly Ser Gly Ala Gly Ala Gly Ser Gly Val Gly Val
  1               5                  10                  15
Pro Gly Val Gly Val Pro Gly Val Gly Val Pro Gly Lys Gly Val Pro
             20                  25                  30
Gly Val Gly Pro Gly Val Gly Pro Gly Val Gly Pro Gly Val Gly Pro
             35                  40                  45
Gly Ala Gly Ala Gly Ser Gly Ala Gly Ala Gly Ser Gly Ala Gly Ala
         50                  55                  60
Gly Ser Gly Ala Gly Ala Gly Ser Gly Val Gly Val Pro Gly Val Gly
 65                  70                  75                  80
Val Pro Gly Val Gly Val Pro Gly Lys Gly Val Pro Gly Val Gly Pro
             85                  90                  95
Gly Val Gly Pro Gly Val Gly Pro Gly Val Gly Pro Gly Ala Gly Ala
             100                 105                 110
Gly Ser Gly Ala Gly Ala Gly Ser Gly Ala Gly Ala Gly Ser Gly Ala
             115                 120                 125
Gly Ala Gly Ser Gly Val Gly Val Pro Gly Val Gly Val Pro Gly Val
         130                 135                 140
Gly Val Pro Gly Lys Gly Val Pro Gly Val Gly Pro Gly Val Gly Pro
145                 150                 155                 160
Gly Val Gly Pro Gly Val Gly Pro Gly Ala Gly Ala Gly Ser Gly Ala
             165                 170                 175
Gly Ala Gly Ser Gly Ala Gly Ala Gly Ser Gly Ala Gly Ala Gly Ser
             180                 185                 190
Gly Val Gly Val Pro Gly Val Gly Val Pro Gly Val Gly Val Pro Gly
         195                 200                 205
Lys Gly Val Pro Gly Val Gly Pro Gly Val Gly Pro Gly Val Gly Pro
210                 215                 220
Gly Val Gly Pro Gly Ala Gly Ala Gly Ser Gly Ala Gly Ala Gly Ser
225                 230                 235                 240
Gly Ala Gly Ala Gly Ser Gly Ala Gly Ala Gly Ser Gly Val Gly Val
             245                 250                 255
Pro Gly Val Gly Val Pro Gly Val Gly Val Pro Gly Lys Gly Val Pro
             260                 265                 270
Gly Val Gly Pro Gly Val Gly Pro Gly Val Gly Pro Gly Val Gly Pro
             275                 280                 285
Gly Ala Gly Ala Gly Ser Gly Ala Gly Ala Gly Ser Gly Ala Gly Ala
             290                 295                 300
Gly Ser Gly Ala Gly Ala Gly Ser Gly Val Gly Val Pro Gly Val Gly
305                 310                 315                 320
Val Pro Gly Val Gly Val Pro Gly Lys Gly Val Pro Gly Val Gly Pro
             325                 330                 335
Gly Val Gly Pro Gly Val Gly Pro Gly Val Gly Pro Gly Ala Gly Ala
             340                 345                 350
Gly Ser Gly Ala Gly Ala Gly Ser Gly Ala Gly Ala Gly Ser Gly Ala
             355                 360                 365
Gly Ala Gly Ser Gly Val Gly Val Pro Gly Val Gly Val Pro Gly Val
         370                 375                 380
Gly Val Pro Gly Lys Gly Val Pro Gly Val Gly Pro Gly Val Gly Pro
385                 390                 395                 400
Gly Val Gly Pro Gly Val Gly Pro Gly Ala Gly Ala Gly Ser Gly Ala
```

-continued

```
                405                 410                 415
Gly Ala Gly Ser Gly Ala Gly Ala Gly Ser Gly Ala Gly Ala Gly Ser
            420                 425                 430
Gly Val Gly Val Pro Gly Val Gly Val Pro Gly Val Gly Val Pro Gly
            435                 440                 445
Lys Gly Val Pro Gly Val Gly Pro Gly Val Gly Pro Gly Val Gly Pro
    450                 455                 460
Gly Val Gly Pro Gly Ala Gly Ala Gly Ser Gly Ala Gly Ala Gly Ser
465                 470                 475                 480
Gly Ala Gly Ala Gly Ser Gly Ala Gly Ala Gly Ser Gly Val Gly Val
                485                 490                 495
Pro Gly Val Gly Val Pro Gly Val Gly Val Pro Gly Lys Gly Val Pro
            500                 505                 510
Gly Val Gly Pro Gly Val Gly Pro Gly Val Gly Pro Gly Val Gly Pro
            515                 520                 525
Gly Ala Gly Ala Gly Ser Gly Ala Gly Ala Gly Ser Gly Ala Gly Ala
            530                 535                 540
Gly Ser Gly Ala Gly Ala Gly Ser Gly Val Gly Val Pro Gly Val Gly
545                 550                 555                 560
Val Pro Gly Val Gly Val Pro Gly Lys Gly Val Pro Gly Val Gly Pro
                565                 570                 575
Gly Val Gly Pro Gly Val Gly Pro Gly Val Gly Pro Gly Ala Gly Ala
            580                 585                 590
Gly Ser Gly Ala Gly Ala Gly Ser Gly Ala Gly Ala Gly Ser Gly Ala
            595                 600                 605
Gly Ala Gly Ser Gly Val Gly Val Pro Gly Val Gly Val Pro Gly Val
            610                 615                 620
Gly Val Pro Gly Lys Gly Val Pro Gly Val Gly Pro Gly Val Gly Pro
625                 630                 635                 640
Gly Val Gly Pro Gly Val Gly Pro Gly Ala Gly Ala Gly Ser Gly Ala
                645                 650                 655
Gly Ala Gly Ser Gly Ala Gly Ala Gly Ser Gly Ala Gly Ala Gly Ser
            660                 665                 670
Gly Val Gly Val Pro Gly Val Gly Val Pro Gly Val Gly Val Pro Gly
            675                 680                 685
Lys Gly Val Pro Gly Val Gly Pro Gly Val Gly Pro Gly Val Gly Pro
    690                 695                 700
Gly Val Gly Pro Gly Ala Gly Ala Gly Ser Gly Ala Gly Ala Gly Ser
705                 710                 715                 720
Gly Ala Gly Ala Gly Ser Gly Ala Gly Ala Gly Ser Gly Val Gly Val
                725                 730                 735
Pro Gly Val Gly Val Pro Gly Val Gly Val Pro Gly Lys Gly Val Pro
            740                 745                 750
Gly Val Gly Pro Gly Val Gly Pro Gly Val Gly Pro Gly Val Gly Pro
            755                 760                 765
Gly Ala Gly Ala Gly Ser Gly Ala Gly Ala Gly Ser
            770                 775                 780
```

<210> SEQ ID NO 20
<211> LENGTH: 64
<212> TYPE: PRT
<213> ORGANISM: Artificial Sequence
<220> FEATURE:
<223> OTHER INFORMATION: Description of Artificial Sequence: Synthetic polymer

<400> SEQUENCE: 20

Gly Val Gly Val Pro Gly Val Gly Val Pro Gly Val Gly Val Pro Gly
1               5                   10                  15
Val Gly Val Pro Gly Glu Gly Val Pro Gly Val Gly Val Pro Gly Val
                20                  25                  30
Gly Val Pro Gly Val Gly Val Pro Gly Ala Gly Ala Gly Ser Gly Ala
            35                  40                  45
Gly Ala Gly Ser Gly Ala Gly Ala Gly Ser Gly Ala Gly Ala Gly Ser
        50                  55                  60

<210> SEQ ID NO 21
<211> LENGTH: 696
<212> TYPE: PRT
<213> ORGANISM: Artificial Sequence
<220> FEATURE:
<223> OTHER INFORMATION: Description of Artificial Sequence: Synthetic
      polymer

<400> SEQUENCE: 21

Gly Ala Gly Ala Gly Ser Gly Ala Gly Ala Gly Ser Gly Ala Gly Ala
1               5                   10                  15
Gly Ser Gly Val Gly Val Pro Gly Val Gly Val Pro Gly Val Gly Val
                20                  25                  30
Pro Gly Lys Gly Val Pro Gly Val Gly Val Pro Gly Val Gly Val Pro
            35                  40                  45
Gly Val Gly Val Pro Gly Val Gly Val Pro Gly Ala Gly Ala Gly Ser
        50                  55                  60
Gly Ala Gly Ala Gly Ser Gly Ala Gly Ala Gly Ser Gly Val Gly Val
65                  70                  75                  80
Pro Gly Val Gly Val Pro Gly Val Gly Val Pro Gly Lys Gly Val Pro
                85                  90                  95
Gly Val Gly Val Pro Gly Val Gly Val Pro Gly Val Gly Val Pro Gly
                100                 105                 110
Val Gly Val Pro Gly Ala Gly Ala Gly Ser Gly Ala Gly Ala Gly Ser
            115                 120                 125
Gly Ala Gly Ala Gly Ser Gly Val Gly Val Pro Gly Val Gly Val Pro
        130                 135                 140
Gly Val Gly Val Pro Gly Lys Gly Val Pro Gly Val Gly Val Pro Gly
145                 150                 155                 160
Val Gly Val Pro Gly Val Gly Val Pro Gly Val Gly Val Pro Gly Ala
                165                 170                 175
Gly Ala Gly Ser Gly Ala Gly Ala Gly Ser Gly Ala Gly Ala Gly Ser
                180                 185                 190
Gly Val Gly Val Pro Gly Val Gly Val Pro Gly Val Gly Val Pro Gly
            195                 200                 205
Lys Gly Val Pro Gly Val Gly Val Pro Gly Val Gly Val Pro Gly Val
        210                 215                 220
Gly Val Pro Gly Val Gly Val Pro Gly Ala Gly Ala Gly Ser Gly Ala
225                 230                 235                 240
Gly Ala Gly Ser Gly Ala Gly Ala Gly Ser Gly Val Gly Val Pro Gly
                245                 250                 255
Val Gly Val Pro Gly Val Gly Val Pro Gly Lys Gly Val Pro Gly Val
                260                 265                 270
Gly Val Pro Gly Val Gly Val Pro Gly Val Gly Val Pro Gly Val Gly
            275                 280                 285

```
Val Pro Gly Ala Gly Ala Gly Ser Gly Ala Gly Ala Gly Ser Gly Ala
    290                 295                 300
Gly Ala Gly Ser Gly Val Gly Val Pro Gly Val Gly Val Pro Gly Val
305                 310                 315                 320
Gly Val Pro Gly Lys Gly Val Pro Gly Val Gly Val Pro Gly Val Gly
                325                 330                 335
Val Pro Gly Val Gly Val Pro Gly Val Gly Val Pro Gly Ala Gly Ala
            340                 345                 350
Gly Ser Gly Ala Gly Ala Gly Ser Gly Ala Gly Ala Gly Ser Gly Val
        355                 360                 365
Gly Val Pro Gly Val Gly Val Pro Gly Val Gly Val Pro Gly Lys Gly
    370                 375                 380
Val Pro Gly Val Gly Val Pro Gly Val Gly Val Pro Gly Val Gly Val
385                 390                 395                 400
Pro Gly Val Gly Val Pro Gly Ala Gly Ala Gly Ser Gly Ala Gly Ala
                405                 410                 415
Gly Ser Gly Ala Gly Ala Gly Ser Gly Val Gly Val Pro Gly Val Gly
            420                 425                 430
Val Pro Gly Val Gly Val Pro Gly Lys Gly Val Pro Gly Val Gly Val
        435                 440                 445
Pro Gly Val Gly Val Pro Gly Val Gly Val Pro Gly Val Gly Val Pro
    450                 455                 460
Gly Ala Gly Ala Gly Ser Gly Ala Gly Ala Gly Ser Gly Ala Gly Ala
465                 470                 475                 480
Gly Ser Gly Val Gly Val Pro Gly Val Gly Val Pro Gly Val Gly Val
                485                 490                 495
Pro Gly Lys Gly Val Pro Gly Val Gly Val Pro Gly Val Gly Val Pro
            500                 505                 510
Gly Val Gly Val Pro Gly Val Gly Val Pro Gly Ala Gly Ala Gly Ser
        515                 520                 525
Gly Ala Gly Ala Gly Ser Gly Ala Gly Ala Gly Ser Gly Val Gly Val
    530                 535                 540
Pro Gly Val Gly Val Pro Gly Val Gly Val Pro Gly Lys Gly Val Pro
545                 550                 555                 560
Gly Val Gly Val Pro Gly Val Gly Val Pro Gly Val Gly Val Pro Gly
                565                 570                 575
Val Gly Val Pro Gly Ala Gly Ala Gly Ser Gly Ala Gly Ala Gly Ser
            580                 585                 590
Gly Ala Gly Ala Gly Ser Gly Val Gly Val Pro Gly Val Gly Val Pro
        595                 600                 605
Gly Val Gly Val Pro Gly Lys Gly Val Pro Gly Val Gly Val Pro Gly
    610                 615                 620
Val Gly Val Pro Gly Val Gly Val Pro Gly Val Gly Val Pro Gly Ala
625                 630                 635                 640
Gly Ala Gly Ser Gly Ala Gly Ala Gly Ser Gly Ala Gly Ala Gly Ser
                645                 650                 655
Gly Val Gly Val Pro Gly Val Gly Val Pro Gly Val Gly Val Pro Gly
            660                 665                 670
Lys Gly Val Pro Gly Val Gly Val Pro Gly Val Gly Val Pro Gly Val
        675                 680                 685
Gly Val Pro Gly Val Gly Val Pro
    690                 695
```

```
<210> SEQ ID NO 22
<211> LENGTH: 1008
<212> TYPE: PRT
<213> ORGANISM: Artificial Sequence
<220> FEATURE:
<223> OTHER INFORMATION: Description of Artificial Sequence: Synthetic
      polymer

<400> SEQUENCE: 22

Gly Ala His Gly Pro Ala Gly Pro Lys Gly Ala His Gly Pro Ala Gly
 1               5                  10                  15

Pro Lys Gly Ala Gln Gly Pro Ala Gly Pro Gly Gly Ala Gln Gly Pro
                20                  25                  30

Ala Gly Pro Gly Gly Ala Gln Gly Pro Ala Gly Pro Gly Gly Ala Gln
                35                  40                  45

Gly Pro Ala Gly Pro Gly Gly Ala Gln Gly Pro Ala Gly Pro Gly Gly
            50                  55                  60

Ala Gln Gly Pro Ala Gly Pro Gly Gly Ala Gln Gly Pro Ala Gly Pro
65                  70                  75                  80

Gly Gly Ala Gln Gly Pro Ala Gly Pro Gly Gly Ala Gln Gly Pro Ala
                85                  90                  95

Gly Pro Gly Gly Ala Gln Gly Pro Ala Gly Pro Gly Gly Ala Gln Gly
                100                 105                 110

Pro Ala Gly Pro Gly Gly Ala Gln Gly Pro Ala Gly Pro Gly Gly Ala
            115                 120                 125

Gln Gly Pro Ala Gly Pro Gly Gly Ala Gln Gly Pro Ala Gly Pro Gly
130                 135                 140

Gly Ala Gln Gly Pro Ala Gly Pro Gly Gly Ala Gln Gly Pro Ala Gly
145                 150                 155                 160

Pro Gly Gly Ala Gln Gly Pro Ala Gly Pro Gly Gly Ala Gln Gly Pro
                165                 170                 175

Ala Gly Pro Gly Gly Ala Gln Gly Pro Ala Gly Pro Gly Gly Ala Gln
            180                 185                 190

Gly Pro Ala Gly Pro Gly Gly Ala Gln Gly Pro Ala Gly Pro Gly Gly
            195                 200                 205

Ala Gln Gly Pro Ala Gly Pro Gly Gly Ala Gln Gly Pro Ala Gly Pro
210                 215                 220

Gly Gly Ala Gln Gly Pro Ala Gly Pro Gly Gly Ala His Gly Pro Ala
225                 230                 235                 240

Gly Pro Lys Gly Ala His Gly Pro Ala Gly Pro Lys Gly Ala His Gly
                245                 250                 255

Pro Ala Gly Pro Lys Gly Ala His Gly Pro Ala Gly Pro Lys Gly Ala
                260                 265                 270

Gln Gly Pro Ala Gly Pro Gly Gly Ala Gln Gly Pro Ala Gly Pro Gly
            275                 280                 285

Gly Ala Gln Gly Pro Ala Gly Pro Gly Gly Ala Gln Gly Pro Ala Gly
        290                 295                 300

Pro Gly Gly Ala Gln Gly Pro Ala Gly Pro Gly Gly Ala Gln Gly Pro
305                 310                 315                 320

Ala Gly Pro Gly Gly Ala Gln Gly Pro Ala Gly Pro Gly Gly Ala Gln
            325                 330                 335

Gly Pro Ala Gly Pro Gly Gly Ala Gln Gly Pro Ala Gly Pro Gly Gly
            340                 345                 350

Ala Gln Gly Pro Ala Gly Pro Gly Gly Ala Gln Gly Pro Ala Gly Pro
            355                 360                 365
```

-continued

```
Gly Gly Ala Gln Gly Pro Ala Gly Pro Gly Gly Ala Gln Gly Pro Ala
        370                 375                 380
Gly Pro Gly Gly Ala Gln Gly Pro Ala Gly Pro Gly Gly Ala Gln Gly
385                 390                 395                 400
Pro Ala Gly Pro Gly Gly Ala Gln Gly Pro Ala Gly Pro Gly Gly Ala
                405                 410                 415
Gln Gly Pro Ala Gly Pro Gly Gly Ala Gln Gly Pro Ala Gly Pro Gly
            420                 425                 430
Gly Ala Gln Gly Pro Ala Gly Pro Gly Gly Ala Gln Gly Pro Ala Gly
        435                 440                 445
Pro Gly Gly Ala Gln Gly Pro Ala Gly Pro Gly Gly Ala Gln Gly Pro
    450                 455                 460
Ala Gly Pro Gly Gly Ala Gln Gly Pro Ala Gly Pro Gly Gly Ala Gln
465                 470                 475                 480
Gly Pro Ala Gly Pro Gly Gly Ala His Gly Pro Ala Gly Pro Lys Gly
                485                 490                 495
Ala His Gly Pro Ala Gly Pro Lys Gly Ala His Gly Pro Ala Gly Pro
            500                 505                 510
Lys Gly Ala His Gly Pro Ala Gly Pro Lys Gly Ala Gln Gly Pro Ala
        515                 520                 525
Gly Pro Gly Gly Ala Gln Gly Pro Ala Gly Pro Gly Gly Ala Gln Gly
    530                 535                 540
Pro Ala Gly Pro Gly Gly Ala Gln Gly Pro Ala Gly Pro Gly Gly Ala
545                 550                 555                 560
Gln Gly Pro Ala Gly Pro Gly Gly Ala Gln Gly Pro Ala Gly Pro Gly
                565                 570                 575
Gly Ala Gln Gly Pro Ala Gly Pro Gly Gly Ala Gln Gly Pro Ala Gly
            580                 585                 590
Pro Gly Gly Ala Gln Gly Pro Ala Gly Pro Gly Gly Ala Gln Gly Pro
        595                 600                 605
Ala Gly Pro Gly Gly Ala Gln Gly Pro Ala Gly Pro Gly Gly Ala Gln
    610                 615                 620
Gly Pro Ala Gly Pro Gly Gly Ala Gln Gly Pro Ala Gly Pro Gly Gly
625                 630                 635                 640
Ala Gln Gly Pro Ala Gly Pro Gly Gly Ala Gln Gly Pro Ala Gly Pro
                645                 650                 655
Gly Gly Ala Gln Gly Pro Ala Gly Pro Gly Gly Ala Gln Gly Pro Ala
            660                 665                 670
Gly Pro Gly Gly Ala Gln Gly Pro Ala Gly Pro Gly Gly Ala Gln Gly
        675                 680                 685
Pro Ala Gly Pro Gly Gly Ala Gln Gly Pro Ala Gly Pro Gly Gly Ala
    690                 695                 700
Gln Gly Pro Ala Gly Pro Gly Gly Ala Gln Gly Pro Ala Gly Pro Gly
705                 710                 715                 720
Gly Ala Gln Gly Pro Ala Gly Pro Gly Gly Ala Gln Gly Pro Ala Gly
                725                 730                 735
Pro Gly Gly Ala His Gly Pro Ala Gly Pro Lys Gly Ala His Gly Pro
            740                 745                 750
Ala Gly Pro Lys Gly Ala His Gly Pro Ala Gly Pro Lys Gly Ala His
        755                 760                 765
Gly Pro Ala Gly Pro Lys Gly Ala Gln Gly Pro Ala Gly Pro Gly Gly
    770                 775                 780
```

-continued

Ala Gln Gly Pro Ala Gly Pro Gly Gly Ala Gln Gly Pro Ala Gly Pro
785                 790                 795                 800

Gly Gly Ala Gln Gly Pro Ala Gly Pro Gly Gly Ala Gln Gly Pro Ala
            805                 810                 815

Gly Pro Gly Gly Ala Gln Gly Pro Ala Gly Pro Gly Gly Ala Gln Gly
        820                 825                 830

Pro Ala Gly Pro Gly Gly Ala Gln Gly Pro Ala Gly Pro Gly Gly Ala
            835                 840                 845

Gln Gly Pro Ala Gly Pro Gly Gly Ala Gln Gly Pro Ala Gly Pro Gly
850                 855                 860

Gly Ala Gln Gly Pro Ala Gly Pro Gly Gly Ala Gln Gly Pro Ala Gly
865                 870                 875                 880

Pro Gly Gly Ala Gln Gly Pro Ala Gly Pro Gly Gly Ala Gln Gly Pro
            885                 890                 895

Ala Gly Pro Gly Gly Ala Gln Gly Pro Ala Gly Pro Gly Gly Ala Gln
        900                 905                 910

Gly Pro Ala Gly Pro Gly Gly Ala Gln Gly Pro Ala Gly Pro Gly Gly
    915                 920                 925

Ala Gln Gly Pro Ala Gly Pro Gly Gly Ala Gln Gly Pro Ala Gly Pro
930                 935                 940

Gly Gly Ala Gln Gly Pro Ala Gly Pro Gly Gly Ala Gln Gly Pro Ala
945                 950                 955                 960

Gly Pro Gly Gly Ala Gln Gly Pro Ala Gly Pro Gly Gly Ala Gln Gly
            965                 970                 975

Pro Ala Gly Pro Gly Gly Ala Gln Gly Pro Ala Gly Pro Gly Gly Ala
        980                 985                 990

His Gly Pro Ala Gly Pro Lys Gly Ala His Gly Pro Ala Gly Pro Lys
    995                 1000                1005

<210> SEQ ID NO 23
<211> LENGTH: 696
<212> TYPE: PRT
<213> ORGANISM: Artificial Sequence
<220> FEATURE:
<223> OTHER INFORMATION: Description of Artificial Sequence: Synthetic
      polymer

<400> SEQUENCE: 23

Gly Val Gly Val Pro Gly Val Gly Val Pro Gly Val Gly Val Pro Gly
1               5                   10                  15

Val Gly Val Pro Gly Lys Gly Val Pro Gly Val Gly Val Pro Gly Val
            20                  25                  30

Gly Val Pro Gly Val Gly Val Pro Gly Ala Ala Gly Ser Gly Ala
        35                  40                  45

Gly Ala Gly Ser Gly Ala Gly Ala Gly Ser Gly Val Gly Val Pro Gly
    50                  55                  60

Val Gly Val Pro Gly Val Gly Val Pro Gly Val Gly Val Pro Gly Lys
65                  70                  75                  80

Gly Val Pro Gly Val Gly Val Pro Gly Val Gly Val Pro Gly Val Gly
            85                  90                  95

Val Pro Gly Ala Gly Ala Gly Ser Gly Ala Gly Ala Gly Ser Gly Ala
        100                 105                 110

Gly Ala Gly Ser Gly Val Gly Val Pro Gly Val Gly Val Pro Gly Val
    115                 120                 125

Gly Val Pro Gly Val Gly Val Pro Gly Lys Gly Val Pro Gly Val Gly
130                 135                 140

-continued

```
Val Pro Gly Val Gly Val Pro Gly Val Gly Val Pro Gly Ala Gly Ala
145                 150                 155                 160

Gly Ser Gly Ala Gly Ala Gly Ser Gly Ala Gly Ala Gly Ser Gly Val
            165                 170                 175

Gly Val Pro Gly Val Gly Val Pro Gly Val Gly Val Pro Gly Val Gly
            180                 185                 190

Val Pro Gly Lys Gly Val Pro Gly Val Gly Val Pro Gly Val Gly Val
            195                 200                 205

Pro Gly Val Gly Val Pro Gly Ala Gly Ala Gly Ser Gly Ala Gly Ala
210                 215                 220

Gly Ser Gly Ala Gly Ala Gly Ser Val Gly Val Pro Gly Val Gly
225                 230                 235                 240

Val Pro Gly Val Gly Val Pro Gly Val Gly Val Pro Gly Lys Gly Val
            245                 250                 255

Pro Gly Val Gly Val Pro Gly Val Gly Val Pro Gly Val Gly Val Pro
            260                 265                 270

Gly Ala Gly Ala Gly Ser Gly Ala Gly Ala Gly Ser Gly Ala Gly Ala
            275                 280                 285

Gly Ser Gly Val Gly Val Pro Gly Val Gly Val Pro Gly Val Gly Val
            290                 295                 300

Pro Gly Val Gly Val Pro Gly Lys Gly Val Pro Gly Val Gly Val Pro
305                 310                 315                 320

Gly Val Gly Val Pro Gly Val Gly Val Pro Gly Ala Gly Ala Gly Ser
            325                 330                 335

Gly Ala Gly Ala Gly Ser Gly Ala Gly Ala Gly Ser Gly Val Gly Val
            340                 345                 350

Pro Gly Val Gly Val Pro Gly Val Gly Val Pro Gly Val Gly Val Pro
            355                 360                 365

Gly Lys Gly Val Pro Gly Val Gly Val Pro Gly Val Gly Val Pro Gly
            370                 375                 380

Val Gly Val Pro Gly Ala Gly Ala Gly Ser Gly Ala Gly Ala Gly Ser
385                 390                 395                 400

Gly Ala Gly Ala Gly Ser Gly Val Gly Val Pro Gly Val Gly Val Pro
            405                 410                 415

Gly Val Gly Val Pro Gly Val Gly Val Pro Gly Lys Gly Val Pro Gly
            420                 425                 430

Val Gly Val Pro Gly Val Gly Val Pro Gly Val Gly Val Pro Gly Ala
            435                 440                 445

Gly Ala Gly Ser Gly Ala Gly Ala Gly Ser Gly Ala Gly Ala Gly Ser
            450                 455                 460

Gly Val Gly Val Pro Gly Val Gly Val Pro Gly Val Gly Val Pro Gly
465                 470                 475                 480

Val Gly Val Pro Gly Lys Gly Val Pro Gly Val Gly Val Pro Gly Val
            485                 490                 495

Gly Val Pro Gly Val Gly Val Pro Gly Ala Gly Ala Gly Ser Gly Ala
            500                 505                 510

Gly Ala Gly Ser Gly Ala Gly Ala Gly Ser Gly Val Gly Val Pro Gly
            515                 520                 525

Val Gly Val Pro Gly Val Gly Val Pro Gly Val Gly Val Pro Gly Lys
            530                 535                 540

Gly Val Pro Gly Val Gly Val Pro Gly Val Gly Val Pro Gly Val Gly
545                 550                 555                 560
```

```
Val Pro Gly Ala Gly Ala Gly Ser Gly Ala Gly Ala Gly Ser Gly Ala
                565                 570                 575

Gly Ala Gly Ser Gly Val Gly Val Pro Gly Val Gly Val Pro Gly Val
            580                 585                 590

Gly Val Pro Gly Val Gly Val Pro Gly Lys Gly Val Pro Gly Val Gly
        595                 600                 605

Val Pro Gly Val Gly Val Pro Gly Val Gly Val Pro Gly Ala Gly Ala
    610                 615                 620

Gly Ser Gly Ala Gly Ala Gly Ser Gly Ala Gly Ala Gly Ser Gly Val
625                 630                 635                 640

Gly Val Pro Gly Val Gly Val Pro Gly Val Gly Val Pro Gly Val Gly
            645                 650                 655

Val Pro Gly Lys Gly Val Pro Gly Val Gly Val Pro Gly Val Gly Val
        660                 665                 670

Pro Gly Val Gly Val Pro Gly Ala Gly Ala Gly Ser Gly Ala Gly Ala
    675                 680                 685

Gly Ser Gly Ala Gly Ala Gly Ser
690                 695

<210> SEQ ID NO 24
<211> LENGTH: 780
<212> TYPE: PRT
<213> ORGANISM: Artificial Sequence
<220> FEATURE:
<223> OTHER INFORMATION: Description of Artificial Sequence: Synthetic
      polymer

<400> SEQUENCE: 24

Gly Ala Pro Gly Thr Pro Gly Pro Gln Gly Leu Pro Gly Ser Pro Gly
1               5                   10                  15

Ala Pro Gly Thr Pro Gly Pro Gln Gly Leu Pro Gly Ser Pro Gly Ala
            20                  25                  30

Pro Gly Thr Pro Gly Pro Gln Gly Leu Pro Gly Ser Pro Gly Ala Pro
        35                  40                  45

Gly Thr Pro Gly Pro Gln Gly Leu Pro Gly Ser Pro Gly Ala Pro Gly
    50                  55                  60

Thr Pro Gly Pro Gln Gly Leu Pro Gly Ser Pro Gly Ala Pro Gly Thr
65                  70                  75                  80

Pro Gly Pro Gln Gly Leu Pro Gly Ser Pro Gly Ala Pro Gly Thr Pro
            85                  90                  95

Gly Pro Gln Gly Leu Pro Gly Ser Pro Gly Ala Pro Gly Thr Pro Gly
        100                 105                 110

Pro Gln Gly Leu Pro Gly Ser Pro Gly Ala Pro Gly Thr Pro Gly Pro
    115                 120                 125

Gln Gly Leu Pro Gly Ser Pro Gly Ala Pro Gly Thr Pro Gly Pro Gln
130                 135                 140

Gly Leu Pro Gly Ser Pro Gly Ala Pro Gly Thr Pro Gly Pro Gln Gly
145                 150                 155                 160

Leu Pro Gly Ser Pro Gly Ala Pro Gly Thr Pro Gly Pro Gln Gly Leu
            165                 170                 175

Pro Gly Ser Pro Gly Ala Pro Gly Thr Pro Gly Pro Gln Gly Leu Pro
        180                 185                 190

Gly Ser Pro Gly Ala Pro Gly Thr Pro Gly Pro Gln Gly Leu Pro Gly
    195                 200                 205

Ser Pro Gly Ala Pro Gly Thr Pro Gly Pro Gln Gly Leu Pro Gly Ser
210                 215                 220
```

```
Pro Gly Ala Pro Gly Thr Pro Gly Pro Gln Gly Leu Pro Gly Ser Pro
225                 230                 235                 240

Gly Ala Pro Gly Thr Pro Gly Pro Gln Gly Leu Pro Gly Ser Pro Gly
            245                 250                 255

Ala Pro Gly Thr Pro Gly Pro Gln Gly Leu Pro Gly Ser Pro Gly Ala
        260                 265                 270

Pro Gly Thr Pro Gly Pro Gln Gly Leu Pro Gly Ser Pro Gly Ala Pro
    275                 280                 285

Gly Thr Pro Gly Pro Gln Gly Leu Pro Gly Ser Pro Gly Ala Pro Gly
290                 295                 300

Thr Pro Gly Pro Gln Gly Leu Pro Gly Ser Pro Gly Ala Pro Gly Thr
305                 310                 315                 320

Pro Gly Pro Gln Gly Leu Pro Gly Ser Pro Gly Ala Pro Gly Thr Pro
            325                 330                 335

Gly Pro Gln Gly Leu Pro Gly Ser Pro Gly Ala Pro Gly Thr Pro Gly
        340                 345                 350

Pro Gln Gly Leu Pro Gly Ser Pro Gly Ala Pro Gly Thr Pro Gly Pro
    355                 360                 365

Gln Gly Leu Pro Gly Ser Pro Gly Ala Pro Gly Thr Pro Gly Pro Gln
370                 375                 380

Gly Leu Pro Gly Ser Pro Gly Ala Pro Gly Thr Pro Gly Pro Gln Gly
385                 390                 395                 400

Leu Pro Gly Ser Pro Gly Ala Pro Gly Thr Pro Gly Pro Gln Gly Leu
            405                 410                 415

Pro Gly Ser Pro Gly Ala Pro Gly Thr Pro Gly Pro Gln Gly Leu Pro
        420                 425                 430

Gly Ser Pro Gly Ala Pro Gly Thr Pro Gly Pro Gln Gly Leu Pro Gly
    435                 440                 445

Ser Pro Gly Ala Pro Gly Thr Pro Gly Pro Gln Gly Leu Pro Gly Ser
450                 455                 460

Pro Gly Ala Pro Gly Thr Pro Gly Pro Gln Gly Leu Pro Gly Ser Pro
465                 470                 475                 480

Gly Ala Pro Gly Thr Pro Gly Pro Gln Gly Leu Pro Gly Ser Pro Gly
            485                 490                 495

Ala Pro Gly Thr Pro Gly Pro Gln Gly Leu Pro Gly Ser Pro Gly Ala
        500                 505                 510

Pro Gly Thr Pro Gly Pro Gln Gly Leu Pro Gly Ser Pro Gly Ala Pro
    515                 520                 525

Gly Thr Pro Gly Pro Gln Gly Leu Pro Gly Ser Pro Gly Ala Pro Gly
530                 535                 540

Thr Pro Gly Pro Gln Gly Leu Pro Gly Ser Pro Gly Ala Pro Gly Thr
545                 550                 555                 560

Pro Gly Pro Gln Gly Leu Pro Gly Ser Pro Gly Ala Pro Gly Thr Pro
            565                 570                 575

Gly Pro Gln Gly Leu Pro Gly Ser Pro Gly Ala Pro Gly Thr Pro Gly
        580                 585                 590

Pro Gln Gly Leu Pro Gly Ser Pro Gly Ala Pro Gly Thr Pro Gly Pro
    595                 600                 605

Gln Gly Leu Pro Gly Ser Pro Gly Ala Pro Gly Thr Pro Gly Pro Gln
610                 615                 620

Gly Leu Pro Gly Ser Pro Gly Ala Pro Gly Thr Pro Gly Pro Gln Gly
625                 630                 635                 640
```

```
Leu Pro Gly Ser Pro Gly Ala Pro Gly Thr Pro Gly Pro Gln Gly Leu
                645                 650                 655

Pro Gly Ser Pro Gly Ala Pro Gly Thr Pro Gly Pro Gln Gly Leu Pro
            660                 665                 670

Gly Ser Pro Gly Ala Pro Gly Thr Pro Gly Pro Gln Gly Leu Pro Gly
        675                 680                 685

Ser Pro Gly Ala Pro Gly Thr Pro Gly Pro Gln Gly Leu Pro Gly Ser
    690                 695                 700

Pro Gly Ala Pro Gly Thr Pro Gly Pro Gln Gly Leu Pro Gly Ser Pro
705                 710                 715                 720

Gly Ala Pro Gly Thr Pro Gly Pro Gln Gly Leu Pro Gly Ser Pro Gly
                725                 730                 735

Ala Pro Gly Thr Pro Gly Pro Gln Gly Leu Pro Gly Ser Pro Gly Ala
            740                 745                 750

Pro Gly Thr Pro Gly Pro Gln Gly Leu Pro Gly Ser Pro Gly Ala Pro
        755                 760                 765

Gly Thr Pro Gly Pro Gln Gly Leu Pro Gly Ser Pro
    770                 775                 780

<210> SEQ ID NO 25
<211> LENGTH: 780
<212> TYPE: PRT
<213> ORGANISM: Artificial Sequence
<220> FEATURE:
<223> OTHER INFORMATION: Description of Artificial Sequence: Synthetic
      polymer

<400> SEQUENCE: 25

Gly Ala Pro Gly Ala Pro Gly Ser Gln Gly Ala Pro Gly Leu Gln Gly
1               5                   10                  15

Ala Pro Gly Ala Pro Gly Ser Gln Gly Ala Pro Gly Leu Gln Gly Ala
            20                  25                  30

Pro Gly Ala Pro Gly Ser Gln Gly Ala Pro Gly Leu Gln Gly Ala Pro
        35                  40                  45

Gly Ala Pro Gly Ser Gln Gly Ala Pro Gly Leu Gln Gly Ala Pro Gly
    50                  55                  60

Ala Pro Gly Ser Gln Gly Ala Pro Gly Leu Gln Gly Ala Pro Gly Ala
65                  70                  75                  80

Pro Gly Ser Gln Gly Ala Pro Gly Leu Gln Gly Ala Pro Gly Ala Pro
                85                  90                  95

Gly Ser Gln Gly Ala Pro Gly Leu Gln Gly Ala Pro Gly Ala Pro Gly
            100                 105                 110

Ser Gln Gly Ala Pro Gly Leu Gln Gly Ala Pro Gly Ala Pro Gly Ser
        115                 120                 125

Gln Gly Ala Pro Gly Leu Gln Gly Ala Pro Gly Ala Pro Gly Ser Gln
    130                 135                 140

Gly Ala Pro Gly Leu Gln Gly Ala Pro Gly Ala Pro Gly Ser Gln Gly
145                 150                 155                 160

Ala Pro Gly Leu Gln Gly Ala Pro Gly Ala Pro Gly Ser Gln Gly Ala
                165                 170                 175

Pro Gly Leu Gln Gly Ala Pro Gly Ala Pro Gly Ser Gln Gly Ala Pro
            180                 185                 190

Gly Leu Gln Gly Ala Pro Gly Ala Pro Gly Ser Gln Gly Ala Pro Gly
        195                 200                 205

Leu Gln Gly Ala Pro Gly Ala Pro Gly Ser Gln Gly Ala Pro Gly Leu
    210                 215                 220
```

-continued

```
Gln Gly Ala Pro Gly Ala Pro Gly Ser Gln Gly Ala Pro Gly Leu Gln
225                 230                 235                 240

Gly Ala Pro Gly Ala Pro Gly Ser Gln Gly Ala Pro Gly Leu Gln Gly
            245                 250                 255

Ala Pro Gly Ala Pro Gly Ser Gln Gly Ala Pro Gly Leu Gln Gly Ala
        260                 265                 270

Pro Gly Ala Pro Gly Ser Gln Gly Ala Pro Gly Leu Gln Gly Ala Pro
    275                 280                 285

Gly Ala Pro Gly Ser Gln Gly Ala Pro Gly Leu Gln Gly Ala Pro Gly
290                 295                 300

Ala Pro Gly Ser Gln Gly Ala Pro Gly Leu Gln Gly Ala Pro Gly Ala
305                 310                 315                 320

Pro Gly Ser Gln Gly Ala Pro Gly Leu Gln Gly Ala Pro Gly Ala Pro
            325                 330                 335

Gly Ser Gln Gly Ala Pro Gly Leu Gln Gly Ala Pro Gly Ala Pro Gly
        340                 345                 350

Ser Gln Gly Ala Pro Gly Leu Gln Gly Ala Pro Gly Ala Pro Gly Ser
    355                 360                 365

Gln Gly Ala Pro Gly Leu Gln Gly Ala Pro Gly Ala Pro Gly Ser Gln
370                 375                 380

Gly Ala Pro Gly Leu Gln Gly Ala Pro Gly Ala Pro Gly Ser Gln Gly
385                 390                 395                 400

Ala Pro Gly Leu Gln Gly Ala Pro Gly Ala Pro Gly Ser Gln Gly Ala
            405                 410                 415

Pro Gly Leu Gln Gly Ala Pro Gly Ala Pro Gly Ser Gln Gly Ala Pro
        420                 425                 430

Gly Leu Gln Gly Ala Pro Gly Ala Pro Gly Ser Gln Gly Ala Pro Gly
    435                 440                 445

Leu Gln Gly Ala Pro Gly Ala Pro Gly Ser Gln Gly Ala Pro Gly Leu
450                 455                 460

Gln Gly Ala Pro Gly Ala Pro Gly Ser Gln Gly Ala Pro Gly Leu Gln
465                 470                 475                 480

Gly Ala Pro Gly Ala Pro Gly Ser Gln Gly Ala Pro Gly Leu Gln Gly
            485                 490                 495

Ala Pro Gly Ala Pro Gly Ser Gln Gly Ala Pro Gly Leu Gln Gly Ala
        500                 505                 510

Pro Gly Ala Pro Gly Ser Gln Gly Ala Pro Gly Leu Gln Gly Ala Pro
    515                 520                 525

Gly Ala Pro Gly Ser Gln Gly Ala Pro Gly Leu Gln Gly Ala Pro Gly
530                 535                 540

Ala Pro Gly Ser Gln Gly Ala Pro Gly Leu Gln Gly Ala Pro Gly Ala
545                 550                 555                 560

Pro Gly Ser Gln Gly Ala Pro Gly Leu Gln Gly Ala Pro Gly Ala Pro
            565                 570                 575

Gly Ser Gln Gly Ala Pro Gly Leu Gln Gly Ala Pro Gly Ala Pro Gly
        580                 585                 590

Ser Gln Gly Ala Pro Gly Leu Gln Gly Ala Pro Gly Ala Pro Gly Ser
    595                 600                 605

Gln Gly Ala Pro Gly Leu Gln Gly Ala Pro Gly Ala Pro Gly Ser Gln
610                 615                 620

Gly Ala Pro Gly Leu Gln Gly Ala Pro Gly Ala Pro Gly Ser Gln Gly
625                 630                 635                 640
```

```
Ala Pro Gly Leu Gln Gly Ala Pro Gly Ala Pro Gly Ser Gln Gly Ala
                645                 650                 655

Pro Gly Leu Gln Gly Ala Pro Gly Ala Pro Gly Ser Gln Gly Ala Pro
            660                 665                 670

Gly Leu Gln Gly Ala Pro Gly Ala Pro Gly Ser Gln Gly Ala Pro Gly
        675                 680                 685

Leu Gln Gly Ala Pro Gly Ala Pro Gly Ser Gln Gly Ala Pro Gly Leu
    690                 695                 700

Gln Gly Ala Pro Gly Ala Pro Gly Ser Gln Gly Ala Pro Gly Leu Gln
705                 710                 715                 720

Gly Ala Pro Gly Ala Pro Gly Ser Gln Gly Ala Pro Gly Leu Gln Gly
                725                 730                 735

Ala Pro Gly Ala Pro Gly Ser Gln Gly Ala Pro Gly Leu Gln Gly Ala
            740                 745                 750

Pro Gly Ala Pro Gly Ser Gln Gly Ala Pro Gly Leu Gln Gly Ala Pro
        755                 760                 765

Gly Ala Pro Gly Ser Gln Gly Ala Pro Gly Leu Gln
    770                 775                 780

<210> SEQ ID NO 26
<211> LENGTH: 33
<212> TYPE: PRT
<213> ORGANISM: Artificial Sequence
<220> FEATURE:
<223> OTHER INFORMATION: Description of Artificial Sequence: Synthetic
      polymer

<400> SEQUENCE: 26

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met

<210> SEQ ID NO 27
<211> LENGTH: 21
<212> TYPE: PRT
<213> ORGANISM: Artificial Sequence
<220> FEATURE:
<223> OTHER INFORMATION: Description of Artificial Sequence: Synthetic
      polymer

<400> SEQUENCE: 27

Gly Ala Gly Ala Met Asp Pro Gly Arg Tyr Gln Asp Leu Arg Ser His
1               5                   10                  15

His His His His
            20

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      polymer

<400> SEQUENCE: 28

Met Asp Pro Gly Arg Tyr Gln Asp Leu Arg Ser His His His His His
1               5                   10                  15

His
```

<210> SEQ ID NO 29
<211> LENGTH: 22
<212> TYPE: PRT
<213> ORGANISM: Artificial Sequence
<220> FEATURE:
<223> OTHER INFORMATION: Description of Artificial Sequence: Synthetic
      polymer

<400> SEQUENCE: 29

Met Asp Pro Gly Arg Tyr Gly Leu Ser Ala Gly Arg Tyr His Tyr Gln
1               5                   10                  15

Leu Val Trp Cys Gln Lys
            20

<210> SEQ ID NO 30
<211> LENGTH: 22
<212> TYPE: PRT
<213> ORGANISM: Artificial Sequence
<220> FEATURE:
<223> OTHER INFORMATION: Description of Artificial Sequence: Synthetic
      polymer

<400> SEQUENCE: 30

Met Asp Pro Thr Arg Tyr Gly Leu Ser Ala Gly Arg Tyr His Tyr Gln
1               5                   10                  15

Leu Val Trp Cys Gln Lys
            20

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      polymer

<400> SEQUENCE: 31

Met Asp Pro Gly Arg Tyr Gln Leu Ser Ala Gly Arg Tyr His Tyr Gln
1               5                   10                  15

Leu Val Trp Cys Gln Lys
            20

<210> SEQ ID NO 32
<211> LENGTH: 22
<212> TYPE: PRT
<213> ORGANISM: Artificial Sequence
<220> FEATURE:
<223> OTHER INFORMATION: Description of Artificial Sequence: Synthetic
      polymer

<400> SEQUENCE: 32

Met Asp Pro Thr Arg Tyr Gln Leu Ser Ala Gly Arg Tyr His Tyr Gln
1               5                   10                  15

Leu Val Trp Cys Gln Lys
            20

<210> SEQ ID NO 33
<211> LENGTH: 21
<212> TYPE: PRT
<213> ORGANISM: Artificial Sequence
<220> FEATURE:
<223> OTHER INFORMATION: Description of Artificial Sequence: Synthetic
      polymer

<400> SEQUENCE: 33

-continued

```
Gly Ala Gly Ala Met Asp Pro Gly Arg Tyr Gln Asp Leu Arg Ser His
  1               5                  10                  15
His His His His His
            20

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      polymer

<400> SEQUENCE: 34

Met Asp Pro Gly Arg Tyr Gly Asp Leu Arg Ser His His His His
  1               5                  10                  15
His
```